US012016988B2

(12) United States Patent
Ritter et al.

(10) Patent No.: US 12,016,988 B2
(45) Date of Patent: Jun. 25, 2024

(54) DEVICE FOR EXCHANGING SUBSTANCES BETWEEN BLOOD AND AT LEAST ONE GAS/GAS MIXTURE

(71) Applicant: enmodes GmbH, Aachen (DE)

(72) Inventors: Ilse Philine Ritter, Aachen (DE); Ralf Borchardt, Aachen (DE)

(73) Assignee: ENMODES GBMH, Aachen (DE)

(*) Notice: Subject to any disclaimer, the term of this patent is extended or adjusted under 35 U.S.C. 154(b) by 712 days.

(21) Appl. No.: 17/254,579

(22) PCT Filed: Oct. 29, 2019

(86) PCT No.: PCT/EP2019/079559
§ 371 (c)(1),
(2) Date: Dec. 22, 2020

(87) PCT Pub. No.: WO2020/089244
PCT Pub. Date: May 7, 2020

(65) Prior Publication Data
US 2021/0275734 A1 Sep. 9, 2021

(30) Foreign Application Priority Data
Oct. 29, 2018 (DE) .................. 10 2018 008 459.1

(51) Int. Cl.
A61M 1/16 (2006.01)
B01D 63/02 (2006.01)
(Continued)

(52) U.S. Cl.
CPC ........ A61M 1/1698 (2013.01); A61M 1/1625 (2014.02); A61M 1/1633 (2014.02);
(Continued)

(58) Field of Classification Search
CPC .............. A61M 1/1698; A61M 1/1625; A61M 1/1633; B01D 63/02; B01D 63/031;
(Continued)

(56) References Cited

U.S. PATENT DOCUMENTS 4,038,190 A 7/1977 Baudet et al.
4,861,485 A 8/1989 Fecondini
(Continued)

FOREIGN PATENT DOCUMENTS

DE 28 25 065 A1 12/1979
DE 39 01 446 A1 8/1989
(Continued)

Primary Examiner — John Kim
(74) Attorney, Agent, or Firm — Norris McLaughlin, P.A.

(57) ABSTRACT

A device for mass transfer between blood and at least one gas/gas mixture, includes first and second chambers through which blood is able to flow and in each of which a respective plurality of mass-permeable hollow fibers are disposed around a respective axially extending core element, wherein a gas/gas mixture is able to flow through, and blood is able to flow around, the hollow fibers, wherein the second chamber follows the first chamber in the blood flow direction, wherein the first and second chambers are disposed next to one another, and in particular disposed spaced apart between the core element center axes thereof, and the two chambers have a connection in an axial end region by which the chamber volumes through which blood is able to flow are connected, and in particular are connected in the direction of the spacing.

17 Claims, 12 Drawing Sheets

(51) Int. Cl.
  *B01D 63/04* (2006.01)
  *B01D 63/06* (2006.01)
  *B01D 69/08* (2006.01)
(52) U.S. Cl.
  CPC .......... *B01D 63/02* (2013.01); *B01D 63/031* (2022.08); *B01D 63/032* (2022.08); *B01D 63/04* (2013.01); *B01D 63/043* (2013.01); *B01D 63/065* (2013.01); *B01D 63/069* (2022.08); *B01D 69/08* (2013.01); *B01D 2201/28* (2013.01); *B01D 2259/4533* (2013.01); *B01D 2319/04* (2013.01)
(58) Field of Classification Search
  CPC .... B01D 63/032; B01D 63/04; B01D 63/043; B01D 63/065; B01D 63/069; B01D 69/08; B01D 2201/28; B01D 2259/4533; B01D 2319/04
  See application file for complete search history.

(56) References Cited

U.S. PATENT DOCUMENTS

| | | |
|---|---|---|
| 5,855,201 A | 1/1999 | Fukui et al. |
| 6,315,895 B1 | 11/2001 | Summerton et al. |
| 2004/0127842 A1 | 7/2004 | Collins et al. |
| 2011/0120930 A1 | 5/2011 | Mishkin |
| 2011/0268608 A1* | 11/2011 | Reggiani ............... A61M 1/322 261/6 |
| 2019/0160217 A1 | 5/2019 | Marseille et al. |

FOREIGN PATENT DOCUMENTS

| | | |
|---|---|---|
| DE | 10 2011 018 925 A1 | 10/2012 |
| DE | 10 2015 000 021 A1 | 7/2016 |
| DE | 102016010398 A1 | 12/2017 |
| JP | 2-109572 A | 4/1990 |
| WO | 01/49399 A1 | 7/2001 |
| WO | 2019180088 A1 | 9/2019 |

* cited by examiner

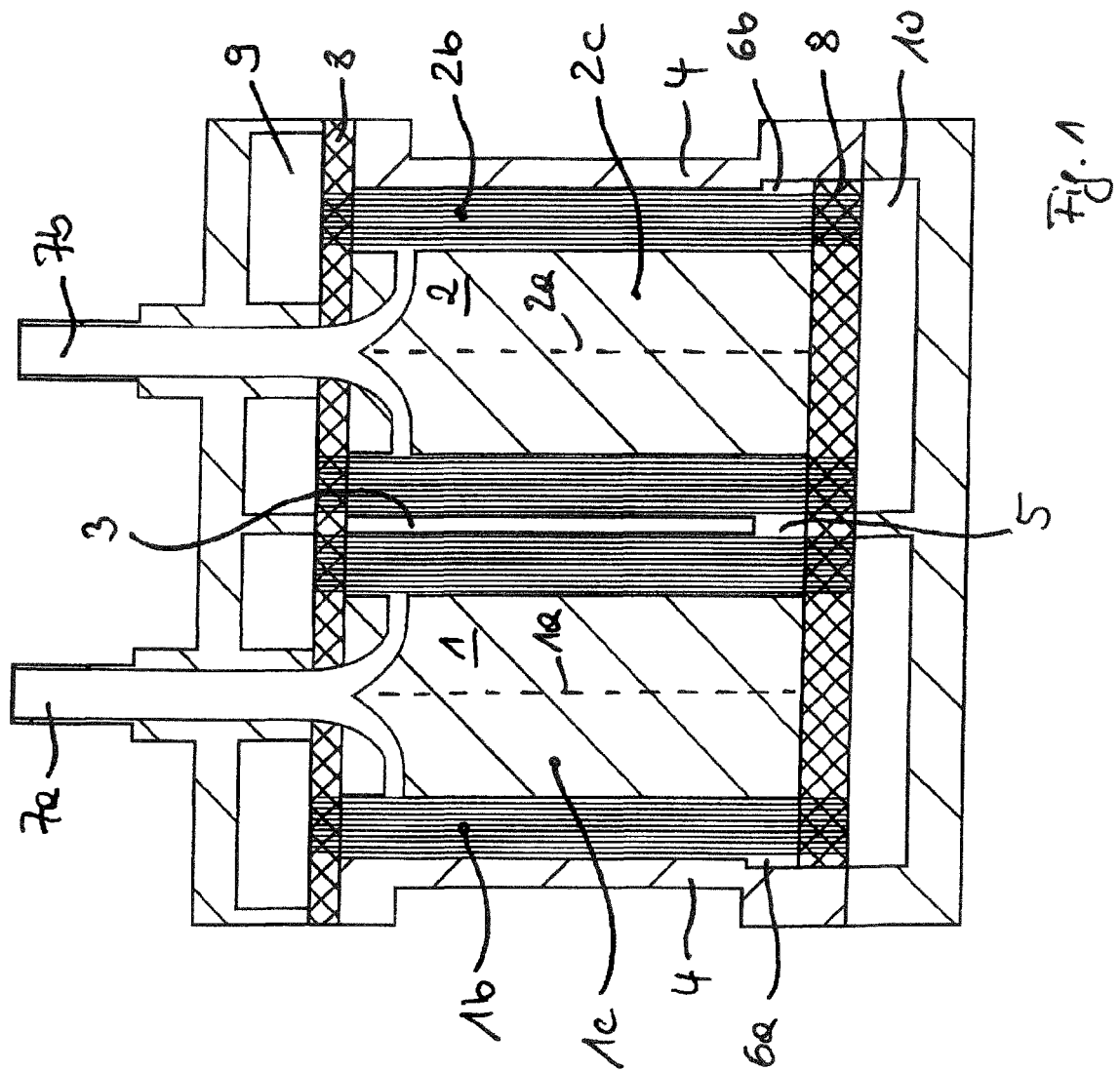

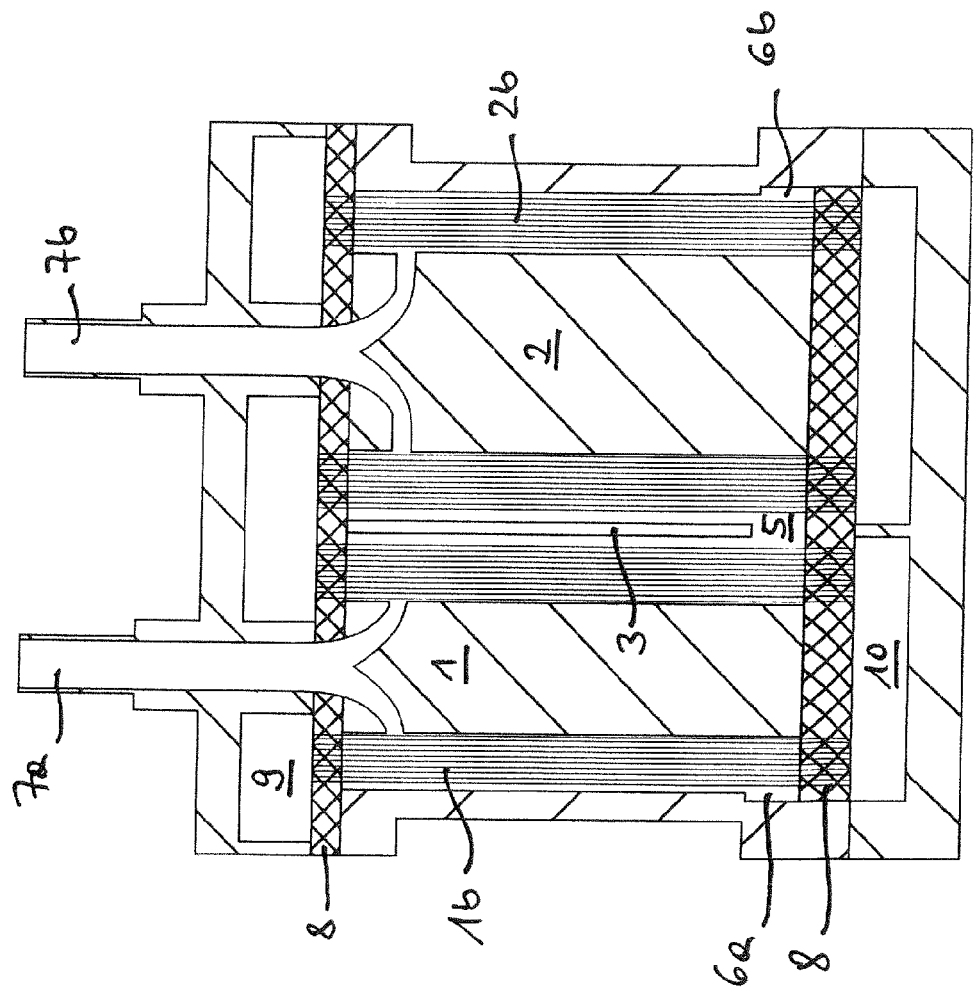

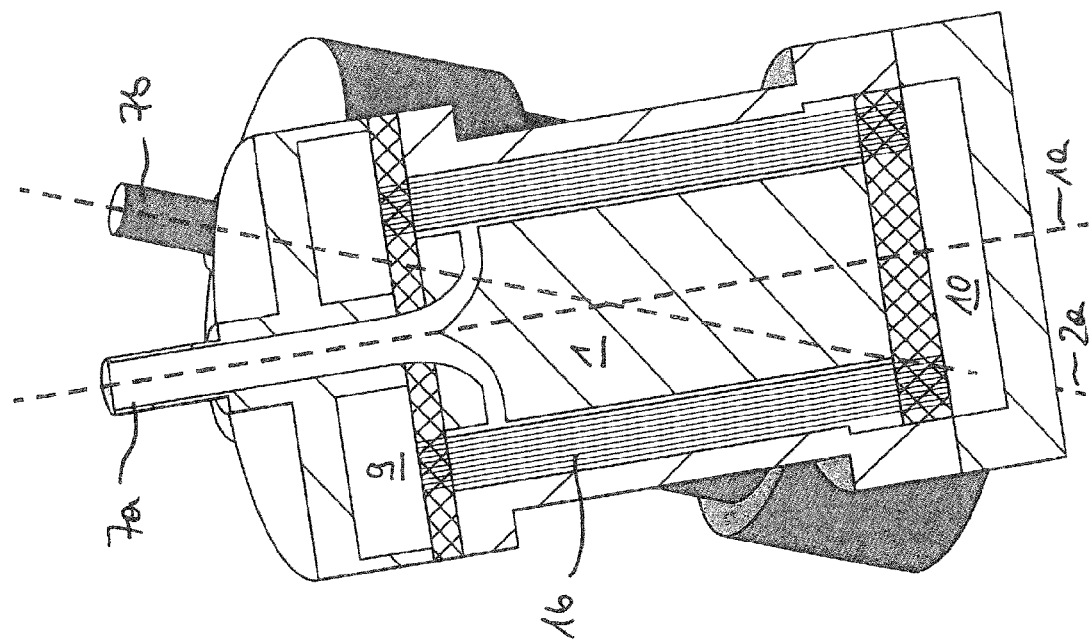

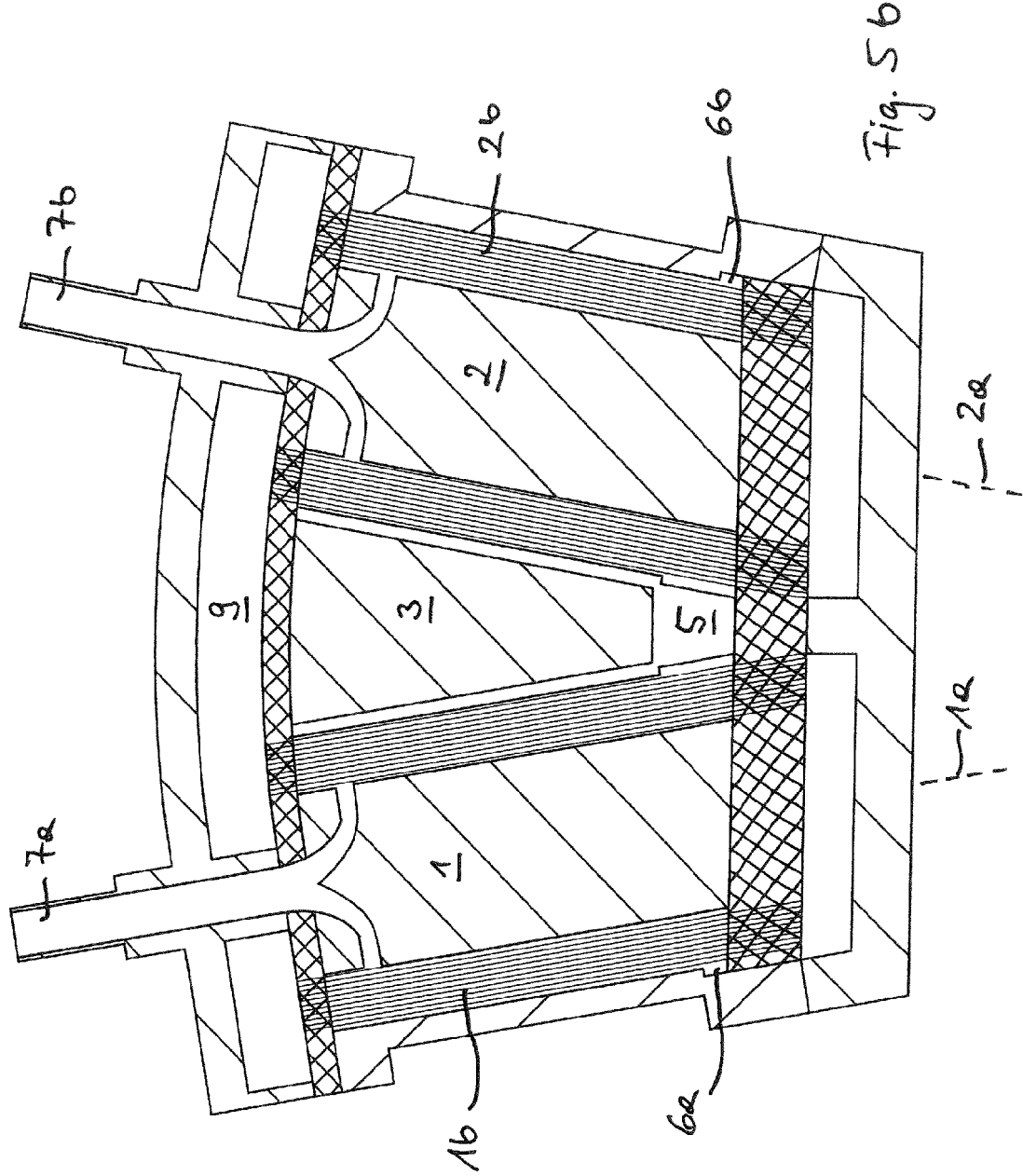

DEVICE FOR EXCHANGING SUBSTANCES BETWEEN BLOOD AND AT LEAST ONE GAS/GAS MIXTURE

BACKGROUND OF THE INVENTION

The invention relates to a device for mass transfer between blood and at least one gas/gas mixture, comprising a first chamber through which blood is able to flow and in which a plurality of mass-permeable hollow fibers are disposed around an axially extending first core element, wherein a gas/gas mixture is able to flow through, and blood is able to flow around, the hollow fibers, and furthermore comprising a second chamber through which blood is able to flow and in which a plurality of mass-permeable hollow fibers are disposed around an axially extending second core element, wherein a gas/gas mixture is able to flow through, and blood is able to flow around, the hollow fibers, wherein the second chamber, in terms of flow, is disposed so as to follow the first chamber in the blood flow direction, in particular which means that blood flowing through the device first flows through the first chamber, and then through the second chamber.

Devices for mass transfer of the type mentioned at the outside are known, in principle, in the prior art and intended, for example, to exchange oxygen and $CO_2$ between the blood and the at least one gas/gas mixture, namely preferably in the sense that the blood in the chamber is enriched with oxygen, and $CO_2$ is removed therefrom. Devices of this mechanism of action are frequently also referred to as oxygenators.

The mechanism of action of such devices for mass transfer is based on differing partial pressures of the substances to be exchanged being present in the hollow fiber through which the gas or the gas mixture flows and the blood, so that the substances that are in imbalance with one another are transferred through the mass-permeable hollow fibers so as to achieve partial pressure equalization.

This is possible due to the mass-permeable design of the hollow fibers, which allows the substances intended to be transferred, such as oxygen and carbon dioxide in this preferred application, to pass through the hollow fiber walls. Blood, in contrast, cannot transfer out of the chamber, through the hollow fiber walls, into the interior of a hollow fiber so that, in principle, the blood-filled chamber and the gas-filled inner regions of the hollow fibers are separated, in terms of the blood, from one another beyond the hollow fiber walls, but in particular, are connected, in terms of the gas components in the blood, beyond the hollow fiber walls. Mass-permeable hollow fibers that allow oxygen and carbon dioxide to transfer, but do not allow other blood components to transfer, are also referred to as semi-permeable.

In devices of the known type, and preferably also in the design according to the invention, hollow fibers disposed next to one another can be joined, for example by way of warp threads, to form mats, whereby the option exists to wind mats comprising such mass-permeable hollow fibers around a core element. The core element preferably forms a winding aid in the process, and also later, when such a device has been installed, represents an element that stabilizes the formed wound roll of hollow fibers.

For example, and also in the invention, the hollow fibers wound onto the core element can preferably be inserted together, in this wound configuration, into a respective chamber. So-called potting, by way of an adhesive, at the axial ends of the chamber yields a volume of the chamber fillable with blood, and the option of having a gas or gas mixture flow against the hollow fibers that are open at the axial ends and extend through the potting adhesive. Here, the hollow fibers are surrounded by the potting adhesive at the axial ends of the chambers. The hollow fibers, with the open ends thereof, extend through the potting adhesive into a gas inlet or gas outlet.

It is essentially known in devices of the type mentioned at the outset to have the blood flow and the gas flow take place at least substantially, that is, preferably at least predominantly, parallel to the axial extension of the chamber or the core element and/or of the hollow fibers, either in a co-current flow or a counterflow, wherein each configuration entails advantages and disadvantages for the effects to be achieved.

A co-current flow operation, for example, has the advantage that, initially, a high concentration gradient results, and thus also, initially, very efficient mass transfer results, but a complete exchange cannot be achieved.

The counterflow operation yields the advantage that complete equalization of the concentration of the substances to be exchanged in the two media is possible, but the counterflow operation is initially inefficient compared to the co-current flow operation.

Moreover, devices of the described type are known in which two respective chambers are used, in which, as described at the outset, mass-permeable hollow fibers are disposed around a respective chamber element, wherein the second chamber, in terms of flow, is disposed so as to follow the first chamber, in the blood flow direction. In principle, in the process, it is possible for a flow of blood and gas to be achieved in a co-current flow in the one chamber, and in a counterflow in the other chamber.

In this known prior art, such two chambers are disposed coaxially inside one another, as a result of which the design, and in particular the assembly, of such a device becomes complicated, in particular since different core and chamber wall elements have to be combined with one another, by being coaxially inserted into one another, and thereafter have to be sealed by potting. A device of this type is known by the designation "Hilite" from Xenios.

SUMMARY OF THE INVENTION

It is thus an object of the invention to provide a device of the type mentioned at the outset, comprising two such chambers, which has a simpler design and preferably a more ergonomic shape compared to the known designs. It is also an object to achieve a more uniform flow of blood through the gas exchanger, and to provide more efficient mass transfer.

This object is achieved according to the invention by disposing the first and second chambers next to one another. In particular, this shall be understood to mean that the center longitudinal axes of the two core elements do not overlap fully, which is to say these do not lie collinearly, and these axes preferably also do not intersect in the space, and in particular at least do not intersect within the device according to the invention.

This can be achieved, for example, by the core element center lines, which preferably coincide with the chamber center lines, in this juxtaposed arrangement according to the invention, having a spacing, for example a radial spacing, everywhere along the axial extension, in particular when the center longitudinal axes extend parallel, for example at a distance.

It is furthermore provided according to the invention that the two chambers have a connection in an axial end region of the respective chamber extensions, by which the chamber volumes through which blood can flow are connected, in particular are connected in the direction of the spacing, and in particular in the radial direction. The connection is preferably located at the same axial height or position with respect to the center lines in both chambers, in particular axially directly in front of the potting adhesive.

An implementation of the device having this design has the advantage over the known designs that the two chambers are not disposed coaxially inside one another, thereby resulting in easier assembly and an overall simpler design since, for the production of the device, all that is essentially necessary is to insert a hollow fiber bundle that is wound onto a first chamber element into the first chamber, and to insert a second hollow fiber bundle that is wound onto a second core element into a second chamber, whereby a relative arrangement of the hollow fiber bundles with respect to one another can be dispensed with.

The connection of the chamber volumes at an axial end region of the two chambers ensures that the blood is able to transfer from the first chamber into the second chamber, and in particular in the process, after the transfer, the flow direction of the blood essentially reverses.

As a result of the connection at an axial end region, which may be formed, for example, by a shared bottom region of a device sitting upright, it can thus be achieved that the blood in such a device flows from the top to the bottom in a first chamber, thereafter crosses over from the first chamber into the second chamber at the lower axial end region, for example in the radial direction, and thereafter flows in the second chamber from the bottom to the top.

In a preferred embodiment, for example, in which the two chambers and the hollow fibers disposed therein and wound onto core elements are designed to be identical with respect to the dimensions thereof, an exactly mirrored blood conduction can be implemented between the two chambers, thereby achieving a considerably more homogeneous treatment, in particular enrichment of the blood with oxygen and removal of carbon dioxide from the blood, compared to the prior art.

The invention preferably provides that a blood inlet into the first chamber and a blood outlet out of the second chamber are disposed on the same side of the device, in particular on the side of the device located opposite the axial end region including the connection between the chambers. As described above, a flow reversal of the blood is thus achieved after the transfer between the chambers, in particular having the aforementioned mirror symmetry, provided the chambers, as mentioned, are identical with respect to the dimensions. The design, however, is preferred insofar as the blood connection can be carried out from above with a standing design.

In a preferred embodiment, the invention furthermore provides that at least one gas inlet and at least one gas outlet are disposed on opposite sides of the device, in particular namely in a manner such that at least one gas inlet is disposed on the side on which the blood inlet and the blood outlet of the device are also positioned, and at least one gas outlet is disposed on the opposite side on which the axial end region including the connection between the chambers is located. The respective open ends of the hollow fibers open into the respective volumes defined by the respective gas inlet and gas outlet, so that, accordingly, the gas inlet and gas outlet are spaced apart from one another in the hollow fiber extension direction, and in particular in the axial direction of the core element.

In this way, it can be achieved that, both in the first chamber and in the second chamber, the gas flow direction with respect to the device is overall identical, for example, namely takes place from the top to the bottom in an oxygenator sitting on the floor, wherein however, as mentioned above, as a result of the blood inlet and blood outlet being disposed on the side located opposite the connection, the blood and the gas/gas mixture are conducted in a co-current flow in the first chamber in the blood flow direction, and the blood and the gas/gas mixture are conducted in a counterflow in the second chamber that follows, in the blood flow direction.

In this way, there is an option of simultaneously employing the co-current flow and counterflow principles during the treatment of blood in a manner that is particularly simple and advantageous, in terms of the design, and in particular thereby open up the respective advantages of the two flow principles in the device.

In one embodiment, the invention can provide that the two chambers have a shared gas inlet and a shared gas outlet. The two chambers, or the hollow fibers disposed therein, are thus supplied, in this design, in the interior thereof with the same gas composition, in particular wherein the same flow velocities are also achieved in the hollow fibers in the two chambers with respect to the gas.

However, another embodiment of the invention can also provide that each of the two chambers is assigned a dedicated pair of gas inlet and gas outlet, in particular wherein in each pair the gas inlet and the gas outlet are also disposed on opposite sides of the device.

Such a chamber-based separation of the conduction of the gases, or the provision of gas connection pairs for each chamber, makes it possible to use a different gas composition in the first chamber compared to the second chamber. In addition to the option of differing compositions of the gas, this also opens up the possibility to set the flow velocities differently in the two chambers.

A design simplification of such a gas flow principle may, for example, result from a respective dedicated gas inlet, but a shared gas outlet, being assigned to each of the two chambers in the device. In this way, it is possible, namely as a result of the separate gas inlets, for each chamber or the hollow fibers thereof to experience individual incident gas flow, wherein the gases having possibly differing compositions, or also differing flow velocities, are mixed on the outlet side and conducted out of the device through the shared gas outlet.

A gas flow can be generated in any arbitrary manner, for example by connecting a gas inlet to a gas cylinder and/or by connecting the outlet to a pump.

The advantage that is essential to the invention was pointed out at the outset, according to which a substantially mirrored treatment of the blood is enabled in the device according to the invention, with the chamber, the hollow fibers, and the core element being designed to have equal dimensions, and in particular identical sizes.

However, the invention can also be such that the first chamber, including the hollow fibers disposed therein on a core element, and the second chamber, including the hollow fibers disposed there on a core element, are designed differently, for example with respect to the dimensions and/or the orientation of the chambers with respect to one another, with the spatial juxtaposition present according to the invention.

For example, the invention can provide that the two chambers have differing diameters, and in particular that the hollow fiber bundles of the two chambers have differing diameters.

A design of the chambers having differing diameters, in particular, has the advantage that the flow profiles can be set differently in the chambers. Ergonomic or design aspects can also play a role here.

As an alternative to or in combination with the aforementioned features, there is also the option of the two chambers having differing axial lengths, and in particular of the hollow fiber bundles of the two chambers having differing axial lengths, however the two chambers preferably have a shared end at the end region including the connection. In a device, as mentioned at the outset, sitting on the floor, the two chambers can thus have a shared lower end, while the upper ends can also be axially spaced with respect to one another, due to the differing lengths.

A design in which the chambers have differing lengths, in particular, has the advantage that, based on the entire transfer length of the device, the change from the co-current flow principle to the counterflow principle can take place at a desired point, which is determined by the respective lengths. In this way, it is also possible to reduce the fiber surface, and increase the efficiency. In addition, it becomes possible to configure the flow profiles in the chambers differently, and to adapt them based on the application. Here as well, ergonomic and design aspects can play a role. It may be provided, for example, that further components are disposed above one of the two chambers, preferably the shorter one.

By designing the device with geometrically different large chambers, regardless of whether this is achieved by differing lengths and/or differing diameters, it is essentially also achieved that the chamber volumes of the first chamber and the second chamber within the device differ, so that differing residence times, and thus differing treatment times for the mass transfer, can result for the blood in the first and second chambers, with the volume flow of the blood remaining the same in the overall device.

In particular an embodiment in which the chambers have at least identical axial lengths, and are preferably disposed parallel with the center lines of the core elements, allows for a further advantage, in terms of the design, in that a shared housing element of the device, in particular a bottom element at the bottom and a cover element at the top, can be used at the axial ends of the device, for the termination of the two chambers.

The invention can, in principle, provide that the center lines of the core elements, in particular thus also the center lines of the chambers, are situated parallel to and spaced apart from one another. In this embodiment according to the invention, the juxtaposition of the two chambers thus results from exact radial spacing of the chambers with respect to one another. In particular, the radial spacing between the two center lines is greater than the sum of the two radii of the respective chambers.

In this way, the chamber inside walls are still spaced apart even at the location at which they approach one another closest, which is to say, on the sides of the chambers facing one another. In this implementation, the chamber volumes accordingly do not overlap and are only connected at the aforementioned axial end region, namely in the preferably radial connecting direction here.

An alternative configuration of the invention may also provide that the center lines of the two chambers are not situated parallel. Viewed in a projection, the center lines can thus intersect in a region between the gas inlet side and the gas outlet side, or the center lines can be situated so as to intersect, viewed in a projection, outside the device, in particular beyond the end including the connection. Although the projection includes a point of intersection, the axes preferably do not, however, in fact, intersect in space.

In a device assumed to be sitting on the floor, the point of intersection of the center lines may thus be located below the bottom region of the device, and thus outside the device.

The design can furthermore be such that, viewed in a first projection, the two center lines intersect and, in a projection perpendicular thereto, the two center lines are located parallel. In particular in this described perpendicular second projection, the two center lines accordingly have a spacing that results in the claimed adjoining arrangement of the chambers. In the described first projection, the two center lines, provided these are situated parallel to one another, can be located aligned behind one another.

In another preferred embodiment, the invention provides, in all possible designs, that an annular space is disposed around the respective hollow fibers of each chamber at the end region including the connection, wherein the two annular spaces of the two chambers overlap in the connecting region. This allows for the possibility that, due to the arrangement of the annular space around the hollow fibers, such an annular space has a larger diameter/cross-section than the diameter/cross-section of the chamber in those areas in which the annular space is not provided. In such an annular space region, the blood, inside the chamber, is thus also able to flow around the outside of the hollow fiber bundle on the particular core element, and to thereby cross over between the chambers with lower flow resistance than would be the case if the blood were only able to flow through the regions between the hollow fibers.

It is particularly preferred that the free cross-section between the hollow fibers and the annular space wall increases in each of the two chambers, in the circumferential direction toward the connecting region, whereby a uniform flow of blood is achieved in the connecting region itself, so that as little shearing forces as possible are exerted on the blood in the connecting region.

It is furthermore possible for the blood to flow from the entire circumference of the hollow fiber bundle in the first chamber into the annular space thereof, and to preferably have the same velocity at all points. Thereafter, the blood can be transferred, preferably without acceleration or deceleration, into the annular space of the second chamber and, from there, is able to uniformly enter the second hollow fiber bundle across the entire circumference. The blood thus preferably does not experience a change in velocity between exiting the first hollow fiber bundle and entering the second hollow fiber bundle. In this way, it is possible to reduce areas of stagnation and flow losses One embodiment can provide that the free cross-section and/or the spacing between the hollow fibers and the annular space wall in the end region increases in each of the two chambers, proceeding from a region, located opposite the connecting region, in particular by 180 degrees, which has the smallest cross-section and/or spacing, clockwise and counter-clockwise to the connecting region.

Another embodiment can provide that the free cross-section and/or the spacing between the hollow fibers and the annular space wall in the end region increases in both chambers, proceeding from the connecting region, in the same direction, in particular clockwise or counter-clockwise, back to the connecting region, or that the free cross-section and/or the spacing between the hollow fibers and the annular space wall in the end region increases, proceeding from the connecting region, clockwise in one of the two chambers, and counter-clockwise in the other chamber, in each case back to the connecting region.

In particular in the latter design, the connecting region can be located laterally offset next to the region having the smallest spacing between the hollow fibers of the two chambers, in a direction perpendicular to the spacing direction of the two chambers. In the process, it may also be provided that a respective annular space in the aforementioned region having the smallest spacing between the hollow fibers of the two chambers has an additional locally delimited taper.

For example, it may be provided in the aforementioned designs that the respective annular space essentially has a circular cross-section, the center of which is offset, and in particular radially offset, with respect to the center line of the core element present in the annular space, in the direction toward the connecting region. Due to the offset, and the resulting acentric arrangement of the annular space and the chamber, an increase in the cross-section of the annular space in the direction toward the connecting region is achieved.

Embodiments of the invention will be described in more detail based on the following figures.

BRIEF DESCRIPTION OF THE DRAWINGS

FIG. 1 shows a preferred embodiment of the invention of an oxygenator device.

FIGS. 4a-4b visualize a design according to the invention in which the chambers 1 and 2 have differing diameters.

FIGS. 5a-5b visualize that the two chambers 1 and 2 can have center lines 1a, 2a that do not extend parallel to one another.

DETAILED DESCRIPTION OF THE INVENTION

Figure 2A:
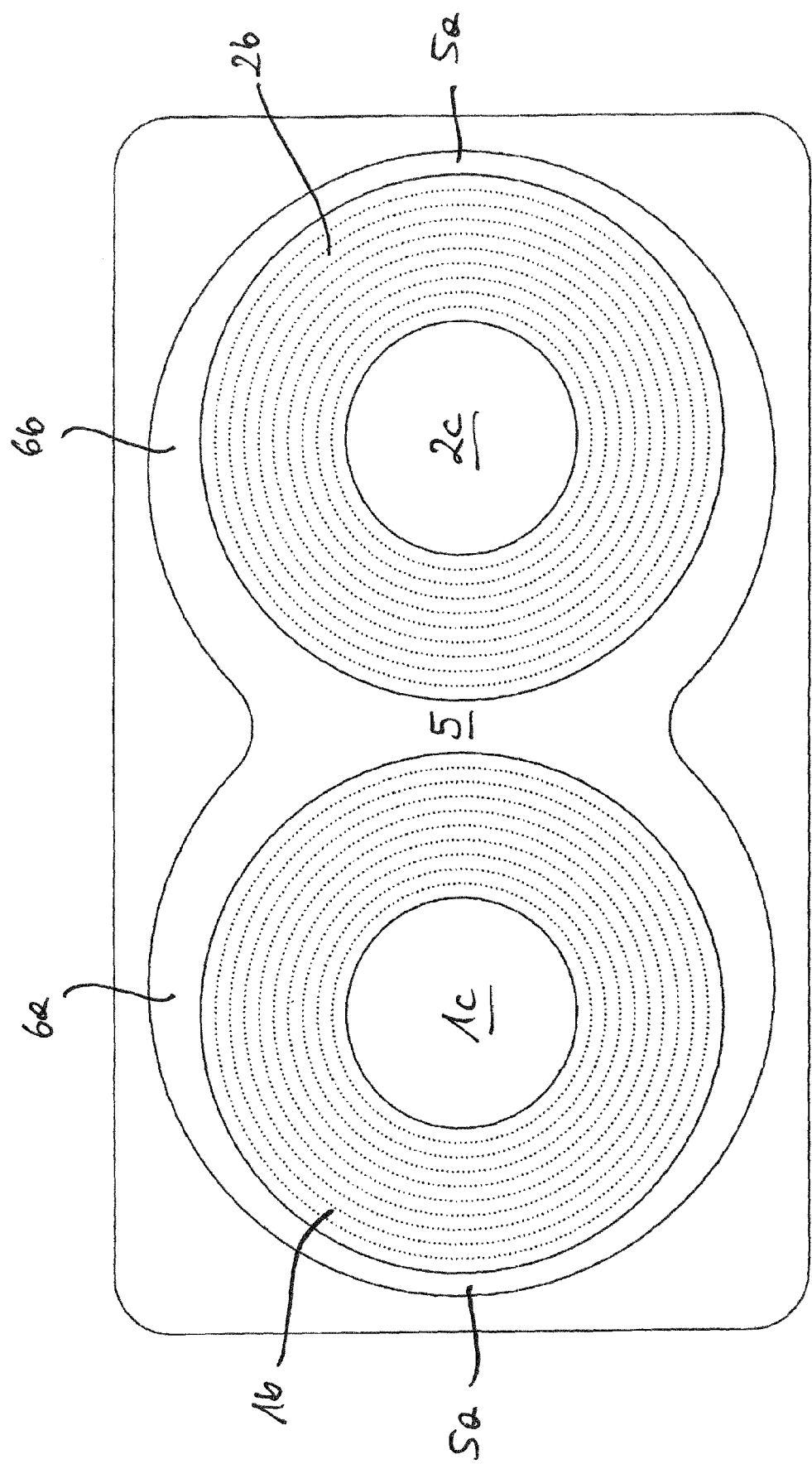
FIGS. 2a-2e each show a sectional illustration of the device according to the invention at the axially lower end 1, with respect to FIG. 1, through the annular spaces 6a and 6b, which surround the hollow fiber bundles 1b and 2b of chamber 1 and chamber 2.

FIG. 1 shows a preferred embodiment of the invention of an oxygenator device, which comprises a first chamber 1 and a second chamber 2. The two chambers have axial center lines 1a and 2a, which in this design are situated parallel to one another and, due to the parallel arrangement, have exact radial spacing with respect to one another, thereby achieving juxtaposition of the first and second chambers. The two chambers 1 and 2 can comprise a shared partition 3 in the interior of the device, which separates the two chamber volumes across the majority of the axial extension, namely with the exception of the connection 5.

The two respective chambers 1 and 2 can, for example, have an inner free cross-section, preferably a circular cross-section, wherein this inner free cross-section in the first chamber 1 is filled with a hollow fiber bundle 1b, which is wound onto a core element 1c, and the inner free cross-section in the second chamber is filled with a hollow fiber bundle 2b, which is wound onto a core element 2c. Across the majority of the axial extension of the first and second chambers, the inner free cross-section can be as large as the outer cross-section of the respective hollow fiber bundle 1b and 1c present in the chamber, so that the hollow fibers, in actuality, are contacted by the chamber walls 4 in the radially outward region, which also form the outer housing walls of the entire device. In this way, blood is not able to flow past the hollow fibers at the radial exterior, apart from in the connecting region 5 mentioned hereafter.

Here at the axially lower end region of the device shown, the chambers 1 and 2 are connected in the radial direction by a connecting region 5, which is disposed axially at the end face before of the lower end of the shared partition 3.

Via this connecting region 5, blood in the chamber 1 here is able to cross, for example from the top to the bottom, at the axially lower end of the chamber 1, over into the chamber 2 in the radial direction, and then flow from the bottom to the top in the second chamber 2.

The connecting region 5 here is essentially formed by a region of overlap between two annular spaces 6a and 6b, which surround the respective hollow fiber bundle 1b or 2b at the axially lower end region of the chambers 1, 2.

FIG. 1 shows a design in which blood is able to flow into the chamber 1 through a blood inlet 7a, which is designed as a hose or tube fitting, for example. In the process, the blood is conducted via the interior of the core element 1c radially to the outside, into the region between the hollow fibers of the hollow fiber bundle 1b, and can flow downwardly here in the axial direction between the hollow fibers of the bundle 1b. After crossing over through the connecting region 5 into the second chamber 2, the blood flows in the axial direction back upward and can, here, in the upper end region of the chamber 2, leave the device via a blood outlet 7b, which is also designed as a tube or hose fitting having a radially interior connection to the chamber volume via the core element.

At the axially opposing sides, the hollow fiber bundles 1b and 2b. are fixedly connected with a potting adhesive 8, wherein the potting adhesive 8 also defines the axial ends of the chambers 1 and 2 with respect to the blood volume.

The hollow fibers extend through the potting adhesive 8 in the axial direction and, in this device, the open ends thereof open into a gas inlet 9 in an axially upper region, and into a gas outlet 10 in a lower region. The two chambers 1 and 2 here each comprise a shared gas inlet 9 and a shared gas outlet 10, so that, in this device, the same gas is conducted from the top to the bottom in the axial direction through the hollow fibers.

Since, in this design, the blood flow in the hollow fiber bundle of chamber 1 is conducted axially from the top to the bottom, and in chamber 2 is conducted from the bottom to the top, guidance between blood and gas is achieved in chamber 1 which corresponds to the co-current flow principle for mass transfer, and which, in chamber 2, corresponds to the counterflow principle for mass transfer between blood and gas. In the device shown here, the blood can thus be treated in a simple manner, in terms of the design, both in a co-current flow and a counterflow, as a result of the juxtaposition of the two chambers, wherein furthermore the dimensional uniformity of chamber 1 and chamber 2 shown here results in an essentially mirror guidance of blood between the two chambers 1 and 2, and thus in a particularly homogeneous treatment of the blood during mass transfer.

FIGS. 2a-2e each show a sectional illustration of the device according to the invention at the axially lower end 1, with respect to FIG. 1, through the annular spaces 6a and 6b, which surround the hollow fiber bundles 1b and 2b of chamber 1 and chamber 2. It is also apparent here that the two annular spaces 6a and 6b can essentially have a ring-like cross-section, in particular a circular cross-section, and, due to the radial spacing thereof, which is smaller than the sum of the two annular space radii, overlap inside the device in such a way that the connecting region 5 or 5' arises, in which the blood is able to cross from chamber 1 over into chamber 2 in a substantially radial direction.

In the region that is axially lower, based on FIG. 1, the blood is able to cross from the hollow fiber bundle 1b in a substantially radial direction over into the annular space 6a, and therein can flow with reduced resistance, compared to the flow between the hollow fibers, in the circumferential direction of the annular space 6a to the connecting region 5, and there can flow into the annular space 6b and be distributed around the hollow fiber bundle 2b, again in the circumferential direction.

It is apparent here that, as a result of the acentric arrangement of the centers, which are not indicated here, of the annular spaces and of the core element center lines, an increase in the cross-sectional area results inside the annular spaces 6a and 6b in the direction toward the connecting region 5, preferably such that the blood flow has a uniform velocity distribution in the overall connecting region.

In the design of FIG. 2a, the free cross-section and/or the spacing between the hollow fibers 1b, 2b and the annular space wall in the end region increases in each of the two chambers 1, 2, proceeding from a region 5a, located opposite the connecting region 5, which has the smallest cross-section and/or spacing, clockwise and counter-clockwise to the connecting region 5.

Figure 2B:
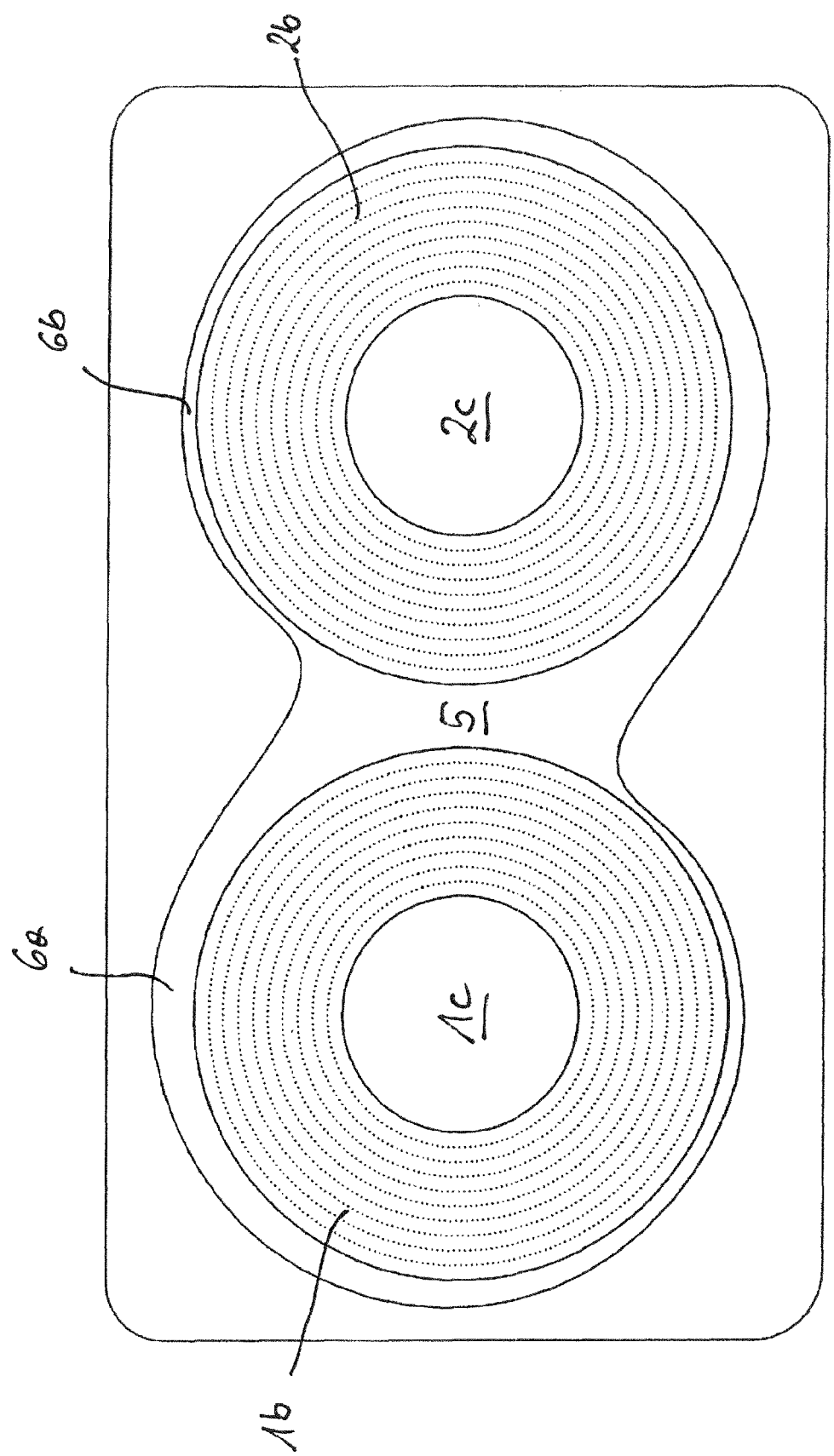

In the design of FIG. 2b, the free cross-section and/or the spacing between the hollow fibers 1b, 2b and the annular space wall in the end region increases in both chambers 1, 2, proceeding from the connecting region 5, in the same direction, this being clockwise here, back to the connecting region 5. The connecting region 5 is disposed about an imaginary line here, which connects the two chamber centers in the spacing direction of the two chambers 1, 2.

Figure 2C:
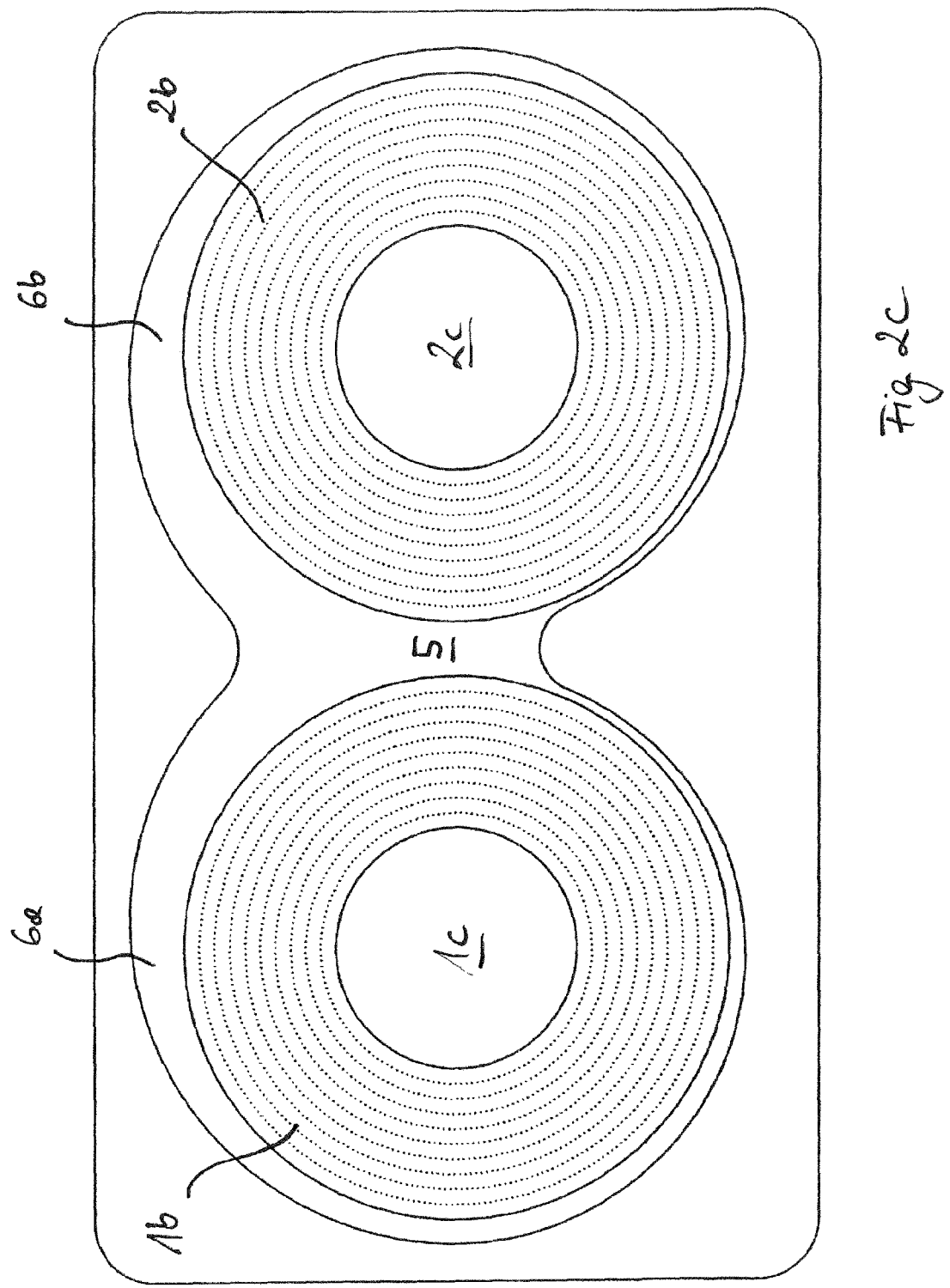
Figure 2D:
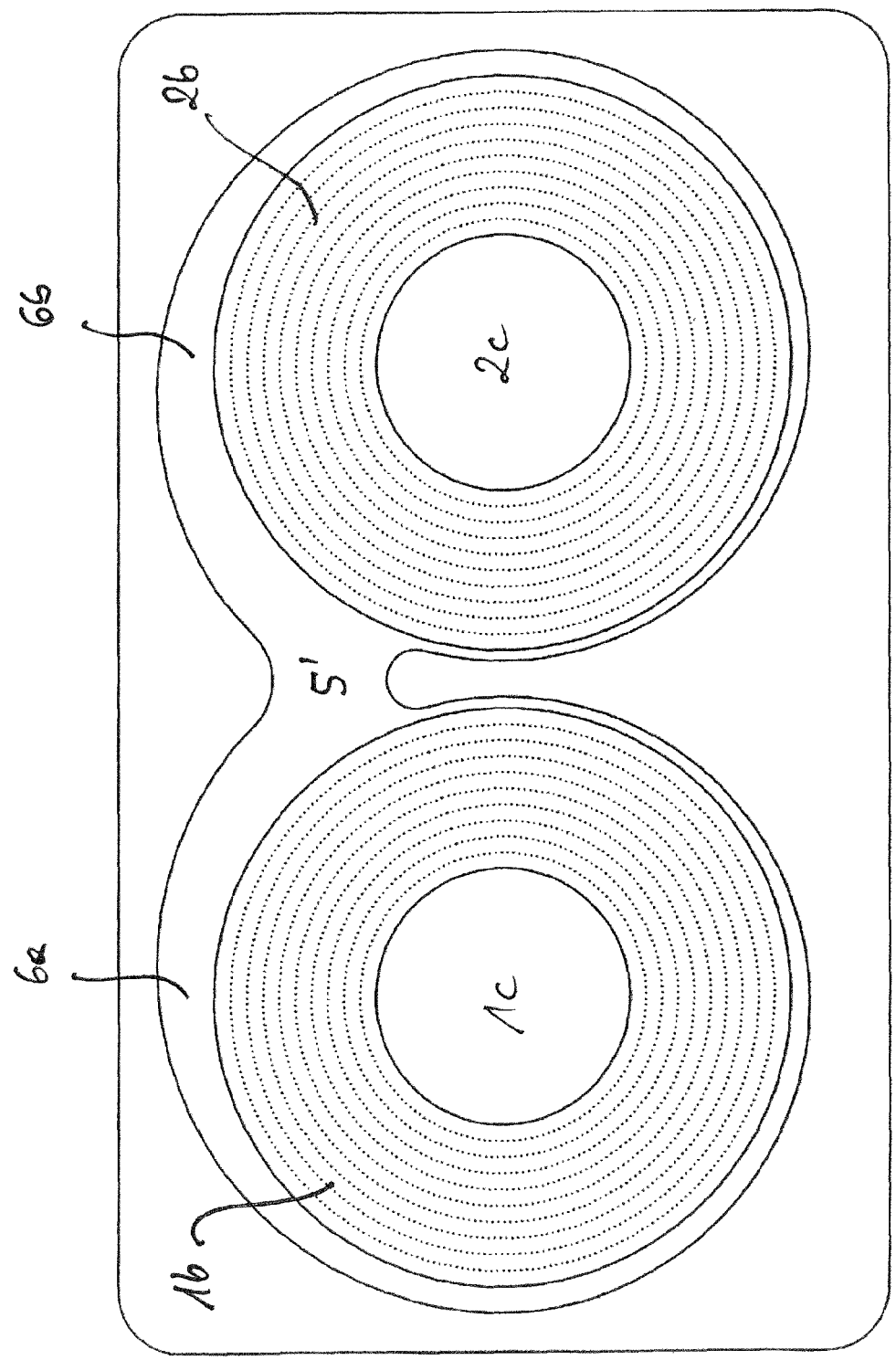

In the design of FIG. 2c, the free cross-section and/or the spacing between the hollow fibers 1b, 2b and the annular space wall in the end region increases, proceeding from the connecting region 5, clockwise in the one chamber 1, and counter-clockwise in the other chamber 2, in each case back to the connecting region 5, and in the variant in FIG. 2d, back to the connecting region 5'. In the designs in FIGS. 2a, c, d and e, the progression of the annular spaces 6a, 6b can preferably be mirror-symmetrical with respect to one another. In the variant in FIG. 2d, the connecting region 5' is located laterally offset next to the region having the smallest spacing between the hollow fibers of the two chambers 1, 2, in a direction perpendicular to the spacing direction of the two chambers 1, 2.

Figure 2E:
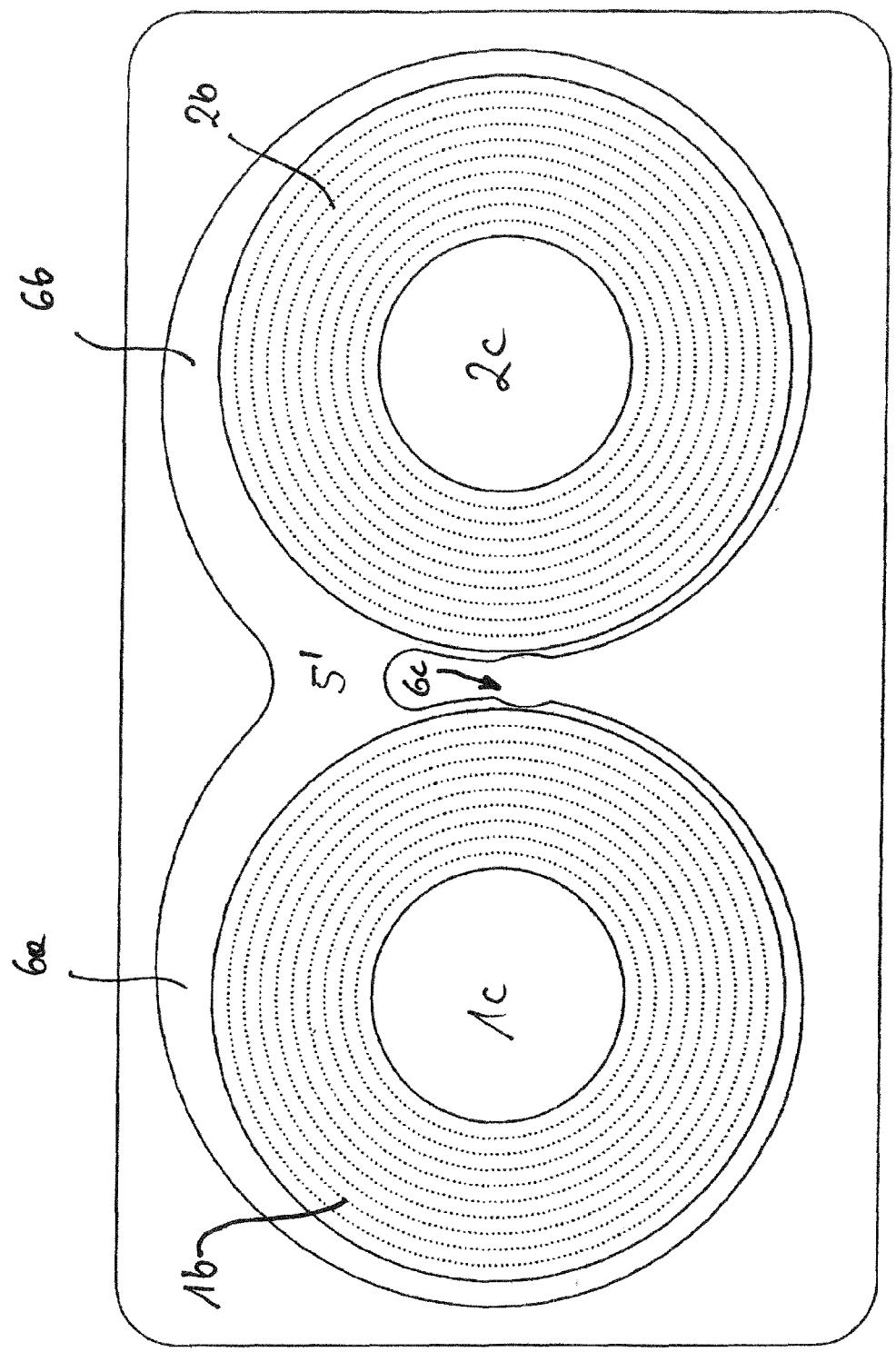

FIG. 2e furthermore shows a possible design based on the design of FIG. 2d, according to which a respective annular space 6a, 6b has an additional locally delimited taper 6c in the region having the smallest spacing between the hollow fibers of the two chambers 1, 2.

Figure 3A:
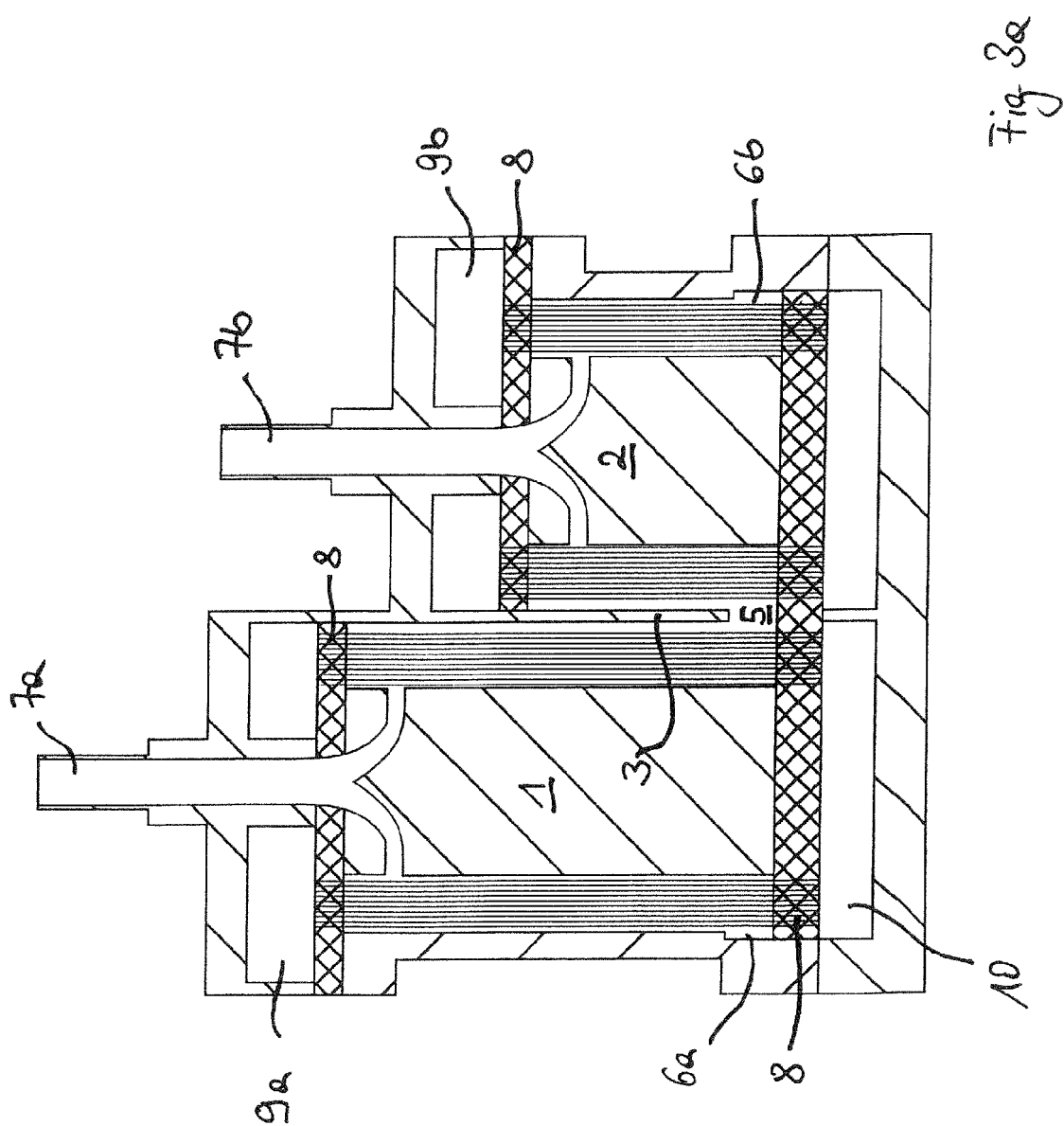
FIG. 3a-3b show another possible embodiments of the invention of an oxygenator device with different axial lengths of chambers 1 and 2.

FIG. 3a shows another possible embodiment of the invention in which, in contrast to the illustration according to FIG. 1, the chamber 1 has a larger axial length than the chamber 2, wherein, however, both chambers 1, 2 have a shared axial end, which is a lower shared axial end here, in which the connecting region 5 is implemented, in particular including the annular spaces 6a, 6b described according to FIG. 2. At the axially upper end regions, the housing of the device, however, has an offset, due to the differing axial lengths of chamber 1 and chamber 2.

Here, it may be provided, for example, that a gas inlet 9a is separate from the gas inlet 9b, so that the two chambers 1, 2 can also be operated with differing gas compositions. The implementation of separate gas inlets can also be provided in the implementation according to FIG. 1. At the end that is axially lower here, a shared gas outlet region 10 is provided, into which the open ends of the hollow fibers in the two chambers 1, 2 open, through potting adhesive 8.

Figure 3B:
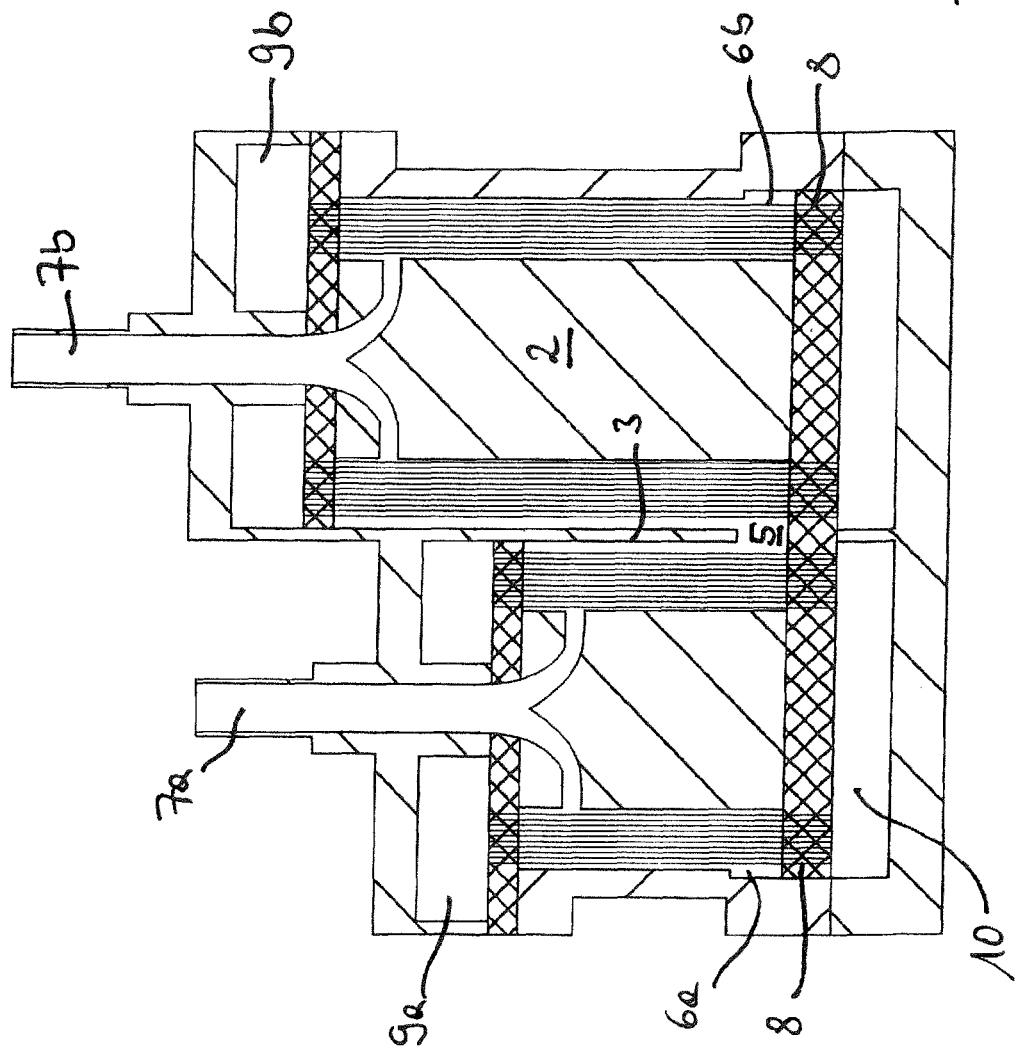

FIG. 3b shows the same device as FIG. 3a, however with the length relationships of the chambers being reversed, which is to say, the axial length of chamber 1 is less than that of chamber 2.

It may furthermore also be provided in the designs of FIGS. 3a and 3b that the gas inlet regions 9a and 9b of the two chambers 1, 2 are fluidically connected, so that the same gas composition is present in both chambers.

Except for the different design of the two chambers 1, 2 axially in terms of the length, the configuration of FIGS. 3a/b can be identical to that of FIG. 1.

Figure 4A:
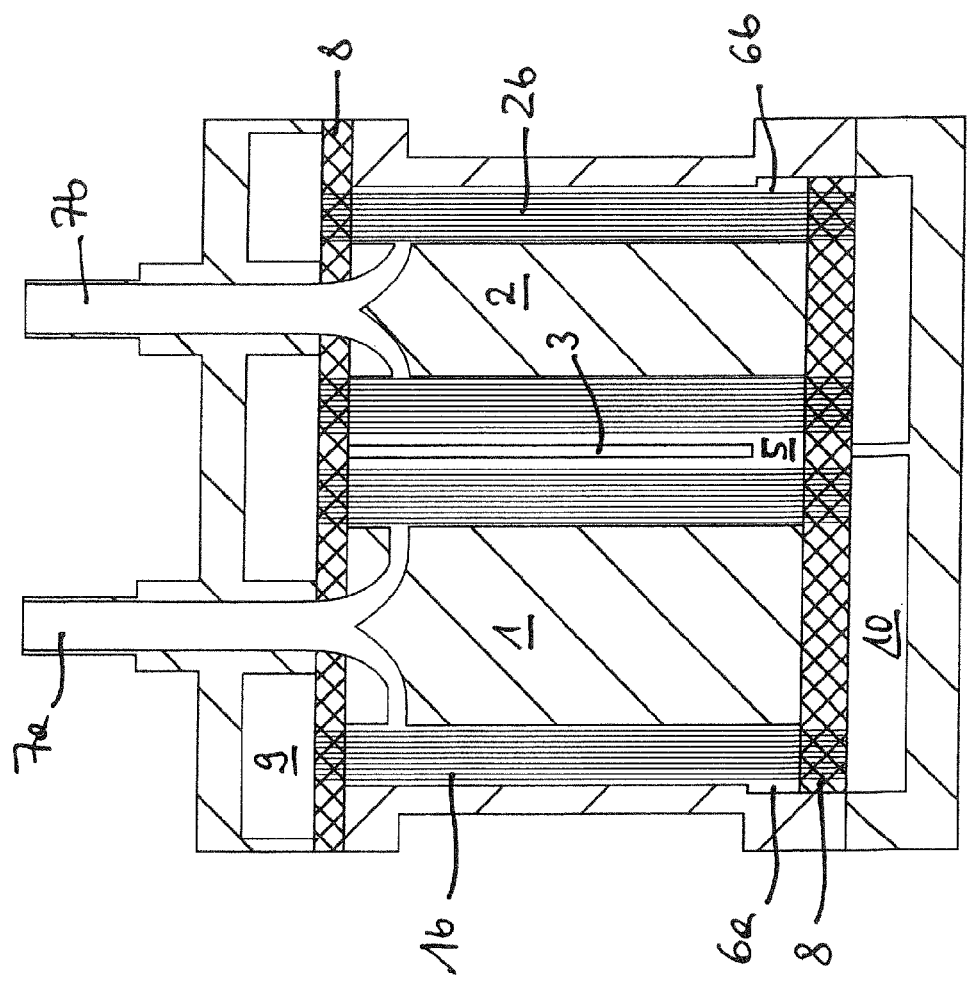

FIGS. 4a, 4b visualize a design according to the invention in which the chambers 1 and 2 have differing diameters. In FIG. 4a, chamber 1 has a smaller diameter compared to chamber 2. The situation is reversed in FIG. 4b. As a result of the differing volumes of the two chambers 1, 2 resulting therefrom, differing flow velocities of the blood can be achieved in these chambers. Otherwise, the designs of FIG. 4 are identical to those of FIGS. 1 and 2.

FIGS. 5a, 5b visualize that the two chambers 1 and 2 can have center lines 1a, 2a that do not extend parallel to one another. According to FIG. 5a, it may be provided that, in the projection illustrated here, the two chamber center lines 1a and 2a intersect inside the device, in particular centrally with respect to the respective axial chamber length.

In FIG. 5b, in contrast, the design is such that the two center lines 1a and 2a, in this projection illustration, likewise intersect, however the point of intersection is located outside, and here beneath, the device according to the invention. In FIG. 5a, the chambers thus essentially have an X configuration, in the projection shown here, whereas the two chambers in FIG. 5b have a V configuration. A partition 3, which has a V-shaped cross-section in this view, can be provided between the two chambers 1 and 2.

In the V configuration, the device can comprise a shared planar bottom region for the two chambers, as is shown here, which simplifies upright positioning of the device.

In a projection that is not shown, which is perpendicular to the top view direction onto the paper plane visualized here, the respective center lines in FIGS. 5a, 5b are spaced apart, whereby the two chambers 1 and 2 are also disposed next to one another according to the invention in this design. In the view shown in FIG. 5a, this means that the chambers 1 and 2 are located behind one another.

The invention claimed is:

1. A device for mass transfer between blood and at least one gas/gas mixture, comprising a first chamber configured for flow of blood therethrough and in which a first bundle of mass-permeable hollow fibers is disposed around an axially extending first core element, the device being configured for flow of a gas/gas mixture through the first bundle of hollow fibers and for flow of blood around the first bundle of hollow fibers, and a second chamber configured for flow of blood therethrough and in which a second bundle of mass-permeable hollow fibers is disposed around an axially extending second core element, the device being configured for flow of a gas/gas mixture through the second bundle of hollow fibers and for flow of blood around the second bundle of hollow fibers, the second chamber being disposed so as to follow the first chamber in a direction of the blood flow, wherein:

the first and second chambers are disposed next to one another with a spacing between respective central axes of the first and second core elements;

the first and the second chambers include a connecting region in an axial end region by which respective interior portions of the first and the second chambers configured for the flow of blood therethrough are connected, and a respective annular space is disposed around each of the first and second bundles of hollow fibers in the respective first and second chambers at the axial end region including the connecting region, the two annular spaces overlapping at the connecting region.

2. The device according to claim 1, further comprising a blood inlet into the first chamber and a blood outlet out of the second chamber, the blood inlet and the blood outlet being disposed on a same side of the device.

3. The device according to claim 1, further comprising at least one gas inlet and at least one gas outlet, the at least one gas inlet and the at least one gas outlet being disposed on opposite sides of the device.

4. The device according to claim 3, wherein one of the gas inlets and one of the gas outlets is shared by the first and the second chambers.

5. The device according to claim 3, wherein each of the first chamber and the second chamber is provided with a respective one of the gas inlets and a respective one of the gas outlets.

6. The device according to claim 3, wherein each of the first chamber and the second chamber is provided with a respective one of the gas inlets and one of the gas outlets is shared by the first and second chambers.

7. The device according to claim 1, wherein the device is configured so that flow of the gas/gas mixture in the first chamber is in the blood flow direction and flow of the gas/gas mixture in the second chamber is counter the blood flow direction.

8. The device according to claim 1, wherein: radial dimension of the respective annular space increases in each of the first chamber and the second chamber in a same circumferential direction or in opposite circumferential directions, and beginning and ending at the connecting region.

9. The device according to claim 8, wherein the radial dimension of the respective annular space in each of the first and the second chambers increases in a circumferential direction opposite to the circumferential direction in which the annular space in the other of the first and the second chambers increases, the connecting region is contiguous with the respective annular space in each of the first and the second chambers where the radial dimension of the respective annular space is smallest and the connecting region is offset in a direction orthogonal to a plane in which the axis of each of the first and second core elements lies.

10. The device according to claim 9, wherein a region of the respective annular space in each of the first and the second chamber at which the radial dimension of the annular space is smallest comprises a radially inward taper of the annular space defining an end of the annular space.

11. The device according to claim 1, wherein each of the first chamber and the second chamber is of a different diameter from the other each of the first hollow fiber bundle and the second hollow fiber bundle is of a different diameter from the other.

12. The device according to claim 11, wherein, viewed in a first projection, the respective center lines of the first and second chambers intersect and, in a projection perpendicular thereto, the respective center lines of the first and second chambers are parallel.

13. The device according to claim 1, wherein each of the first chamber and the second chamber is of a different axial length from the other and each of the first hollow fiber bundle and the second hollow fiber bundle is of a different axial length from the other.

14. The device according to claim 13, wherein the axial end region of each of the first and the second chamber is coplanar with the axial end region of the other.

15. The device according to claim 1, wherein a center line of each of the first chamber and the second chamber is oblique relative to a center line of the other and/or a center line of each of the first core element and the second core element is oblique relative to a center line of the other.

16. The device according to claim 1, wherein the connection is in a direction of the spacing.

17. A device for mass transfer between blood and at least one gas/gas mixture, comprising a first chamber configured for flow of blood therethrough and in which a first bundle of mass-permeable hollow fibers is disposed around an axially extending first core element, the device being configured for flow of a gas/gas mixture through the first bundle of hollow fibers and for flow of blood around the first bundle of hollow fibers, and a second chamber configured for flow of blood therethrough and in which a second bundle of mass-permeable hollow fibers is disposed around an axially extending second core element, the device being configured for flow of a gas/gas mixture through the second bundle of hollow fibers and for flow of blood around the second bundle of hollow fibers, the second chamber being disposed so as to follow the first chamber in a direction of the blood flow, wherein:

the first and second chambers are disposed next to one another;

the first and the second chambers include a connecting region in an axial end region by which respective interior portions of the first and the second chambers configured for the flow of blood therethrough are connected; and a center line of each of the first chamber and the second chamber is oblique relative to a center line of the other and/or a center line of each of the first core element and the second core element is oblique relative to a center line of the other.

* * * * *